US011415574B2

(12) United States Patent
Chirila et al.

(10) Patent No.: US 11,415,574 B2
(45) Date of Patent: Aug. 16, 2022

(54) LYMPHOCYTE-BASED MORPHOMETRIC TEST FOR ALZHEIMER'S DISEASE

(71) Applicant: NeuroDiagnostics LLC, Rockville, MD (US)

(72) Inventors: Florin Valentin Chirila, Morgantown, WV (US); Daniel L. Alkon, Chevy Chase, MD (US)

(73) Assignee: NeuroDiagnostics LLC, Rockville, MD (US)

( * ) Notice: Subject to any disclaimer, the term of this patent is extended or adjusted under 35 U.S.C. 154(b) by 315 days.

(21) Appl. No.: 15/939,948

(22) Filed: Mar. 29, 2018

(65) Prior Publication Data

US 2018/0284103 A1   Oct. 4, 2018

Related U.S. Application Data

(60) Provisional application No. 62/479,630, filed on Mar. 31, 2017.

(51) Int. Cl.
*G01N 33/50* (2006.01)

(52) U.S. Cl.
CPC ..... *G01N 33/5091* (2013.01); *G01N 33/5032* (2013.01); *G01N 33/5052* (2013.01); *G01N 2800/2821* (2013.01); *G01N 2800/50* (2013.01)

(58) Field of Classification Search
CPC ........... G01N 33/5091; G01N 2800/50; G01N 2800/2821; G01N 33/6896; G01N 33/5026; G01N 33/5052; G01N 33/5032
See application file for complete search history.

(56) References Cited

U.S. PATENT DOCUMENTS

| | | | |
|---|---|---|---|
| 6,107,050 A | 8/2000 | Alkon et al. | |
| 7,595,167 B2 | 9/2009 | Khan et al. | |
| 7,682,807 B2 | 3/2010 | Zhao et al. | |
| 7,741,290 B2 | 6/2010 | Mochly-Rosen et al. | |
| 8,658,134 B2 * | 2/2014 | Chirila | G01N 33/6896 424/9.1 |
| 9,188,595 B2 | 11/2015 | Zhao et al. | |
| 9,797,913 B2 | 10/2017 | Khan et al. | |
| 10,317,396 B2 | 6/2019 | Chirila et al. | |
| 2003/0078280 A1 | 4/2003 | Kuo et al. | |
| 2005/0191348 A1 | 9/2005 | Youdim et al. | |
| 2007/0082366 A1 | 4/2007 | Khan et al. | |
| 2009/0029873 A1 | 1/2009 | Khan et al. | |
| 2011/0256565 A1 | 10/2011 | Schon et al. | |
| 2014/0038186 A1 | 2/2014 | Khan et al. | |
| 2014/0235496 A1 | 8/2014 | Alkon et al. | |
| 2014/0329264 A1 | 11/2014 | Chirila et al. | |
| 2017/0023552 A1 | 1/2017 | Chirila et al. | |
| 2018/0282784 A1 | 10/2018 | Chirila et al. | |
| 2019/0041404 A1 | 2/2019 | Chirila et al. | |
| 2019/0331668 A1 | 10/2019 | Chirila et al. | |

FOREIGN PATENT DOCUMENTS

| | | | | |
|---|---|---|---|---|
| JP | 2005532805 A | 11/2005 | | |
| JP | 2009511905 A | 3/2009 | | |
| JP | 2011516883 A | 5/2011 | | |
| JP | 2011529344 A | 12/2011 | | |
| JP | 2013506852 A | 2/2013 | | |
| WO | 2011/041761 A1 | 4/2011 | | |
| WO | 2012/155051 A1 | 11/2012 | | |
| WO | 2013/052922 A1 | 4/2013 | | |
| WO | WO2015103495 A1 * | 7/2015 | ............. | G01N 33/50 |

OTHER PUBLICATIONS

Munoz et al. Enhanced proteasome-dependent degradation of the CDK inhibitor p27kip1 in immortalized lymphocytes from Alzheimer's dementia patients. Neurobiology of Aging 29 (2008) 1474-1484 (Year: 2008).*
Ounanian et al. Characteristics of Epstein-Barr virus transformed B cell lines from patients with Alzheimer's disease and age-matched controls. Mechanisms of Ageing and Development. vol. 63, Issue 1, Mar. 15, 1992, pp. 105-116 (Year: 1992).*
Cuevas et al. Altered transcriptional regulators in response to serum in immortalized lymphocytes from Alzheimer's disease patients. Neurobiology of Aging 26 (2005) 615-624 (Year: 2005).*
Nagy et al. Cell cycle kinesis in lymphocytes in the diagnosis of Alzheimer's disease. Neuroscience Letters 317 (2002) 81-84. (Year: 2002).*
Neron et al. Large-Scale In Vitro Expansion of Polyclonal Human Switched-Memory B Lymphocytes. PLoS ONE 7(12): e51946. (Year: 2012).*

* cited by examiner

*Primary Examiner* — Taeyoon Kim
(74) *Attorney, Agent, or Firm* — Law Offices of Alan J. Morrison (57) ABSTRACT

This invention provides methods for diagnosing Alzheimer's disease in a symptomatic human subject, and for determining whether a human subject is predisposed to becoming afflicted with Alzheimer's disease. These methods employ the steps of (a) culturing a subject's lymphocytes with a suitable basement membrane matrix to permit the lymphocytes to aggregate; (b) measuring the resulting lymphocyte aggregation; and (c) based on such measurement, either diagnosing Alzheimer's disease or determining a predisposition to it, as appropriate.

9 Claims, 5 Drawing Sheets

LYMPHOCYTE-BASED MORPHOMETRIC TEST FOR ALZHEIMER'S DISEASE

This application claims the benefit of U.S. Provisional Application No. 62/479,630, filed Mar. 31, 2017, the contents of which are incorporated herein by reference.

Throughout this application, various publications are cited. The disclosure of these publications is hereby incorporated by reference into this application to describe more fully the state of the art to which this invention pertains.

FIELD OF THE INVENTION

The present invention relates to lymphocyte aggregation-based methods for diagnosing Alzheimer's disease in a human subject, and for determining whether a human subject is predisposed to having Alzheimer's disease.

BACKGROUND OF THE INVENTION

Many data have been collected over the last 15 years indicating that the pathophysiology of Alzheimer's disease is not just related to the brain, but can also have systemic expression. For example, many of the critical amyloid and tau enzymes can be found throughout the body. On this basis, accurate assays have been developed to test skin cells, for example, for Alzheimer's disease against cells from a variety of control patients. Some skin cell-based assays focus on targets such as PKCε and $ERK_{1,2}$.

SUMMARY OF THE INVENTION

This invention provides a method for diagnosing Alzheimer's disease in a symptomatic human subject comprising the steps of (a) culturing lymphocytes from the subject with a suitable basement membrane matrix for a duration and under conditions sufficient to permit the lymphocytes to aggregate; (b) measuring the resulting lymphocyte aggregation; and (c) comparing the measurement of step (b) with a suitable control, thereby determining whether the subject is afflicted with Alzheimer's disease.

This invention also provides a method for determining whether a human subject is predisposed to becoming afflicted with Alzheimer's disease comprising the steps of (a) culturing lymphocytes from the subject with a suitable basement membrane matrix for a duration and under conditions sufficient to permit the lymphocytes to aggregate; (b) measuring the resulting lymphocyte aggregation; and (c) comparing the measurement of step (b) with a suitable control, thereby determining whether the subject is predisposed to becoming afflicted with Alzheimer's disease.

This invention further provides a method for diagnosing Alzheimer's disease in a symptomatic human subject comprising the steps of (a) culturing lymphocytes from the subject with a suitable basement membrane matrix for a duration and under conditions sufficient to permit the lymphocytes to aggregate; (b) measuring the resulting lymphocyte aggregation; and (c) determining whether the measurement of step (b) correlates with Alzheimer's disease in the subject.

Finally, this invention provides a method for determining whether a human subject is predisposed to becoming afflicted with Alzheimer's disease comprising the steps of (a) culturing lymphocytes from the subject with a suitable basement membrane matrix for a duration and under conditions sufficient to permit the lymphocytes to aggregate; (b) measuring the resulting lymphocyte aggregation; and (c) determining whether the measurement of step (b) correlates with the subject's being predisposed to becoming afflicted with Alzheimer's disease.

BRIEF DESCRIPTION OF THE FIGURES

FIG. 1

Increased B lymphocyte aggregation for the Alzheimer's disease case (AD—Panels A, B) compared with the Age-matched Control case (AC—Panels C and D) and a Non-Alzheimer's Demented case (Non-ADD—Panels E and F). Examples of 4× images at 48 hours after plating on a thick layer of Matrigel® (1.82 mm). Panels A, C and E are examples where the cell seeding density is 125 cells/µl, while Panels B, D and F are examples for a cells seeding density of 250 cells/µl.

FIGS. 2A and 2B

% Aggregate Area at 48 hours after plating in 4× images (FIG. 2A) Doubling the seeding cell density from 125 cells/µl to 250 cells/µl results in a larger increase in the % Aggregate Area for the Alzheimer's disease case (AD—blue squares) when compared with Non-Alzheimer's Demented (Non-ADD—green triangles) or Age-matched Control (AC—purple circles).

FIG. 3

Aggregate ranking in 4× images for two cell seeding densities—125 cells/µl and 250 cells/µl Ranking curves in natural logarithmic format, i.e., Ln (Aggregate Area), for the AD case (Panel A) are above the ranking curves for the Non-ADD (Panel B) and AD (panel C) for the two cell seeding densities. (Panel D) Elevated ranking curve for the AD case (purple) compared with the Non-ADD (green) and AC (blue) for the cell seeding density of 125 cells/µl. (Panel E) Elevated ranking curve for AD case (purple) compared with the Non-ADD (green) and AC (blue) for the cell seeding density of 250 cells/µl. (Panel F) The difference between the ranking curves for the two cell seeding densities, i.e., $Ln(Aggregate\ Area)_{250} - Ln(Aggregate\ Area)_{125}$, is elevated for the AD case (purple) in all rankings compared with the Non-ADD (green) and AC (blue).

FIG. 4

Increased B lymphocyte aggregation for the Alzheimer's disease case (AD—Panels A and B) compared with the Age-matched Control case (AC—Panels C and D) and a Non-Alzheimer's Demented case (Non-ADD—Panels E and F). Examples of 10× images at 48 hours after plating on a thick layer of Matrigel® (1.82 mm). Panels A, C and E are examples for the cell seeding density of 125 cells/µl while Panels B, D and F are examples for the cell seeding density of 250 cells/µl.

FIGS. 5A and 5B

% Aggregate Area for 125 and 250 cells/µl at 48 hours after plating in 10× images—better approximation (FIG. 5A, top) Doubling the seeding cell density from 125 cells/µl to 250 cells/µl results in a larger increase in the % Aggregate Area for the Alzheimer's Disease case (AD—blue squares) when compared with Non-Alzheimer's Demented (Non-ADD—green triangles) or Age-matched Control (AC—purple circles). Y-axis=% Aggregate Area; x-axis=cell density (cells/µl).

DETAILED DESCRIPTION OF THE INVENTION

Definitions

Figure 1:
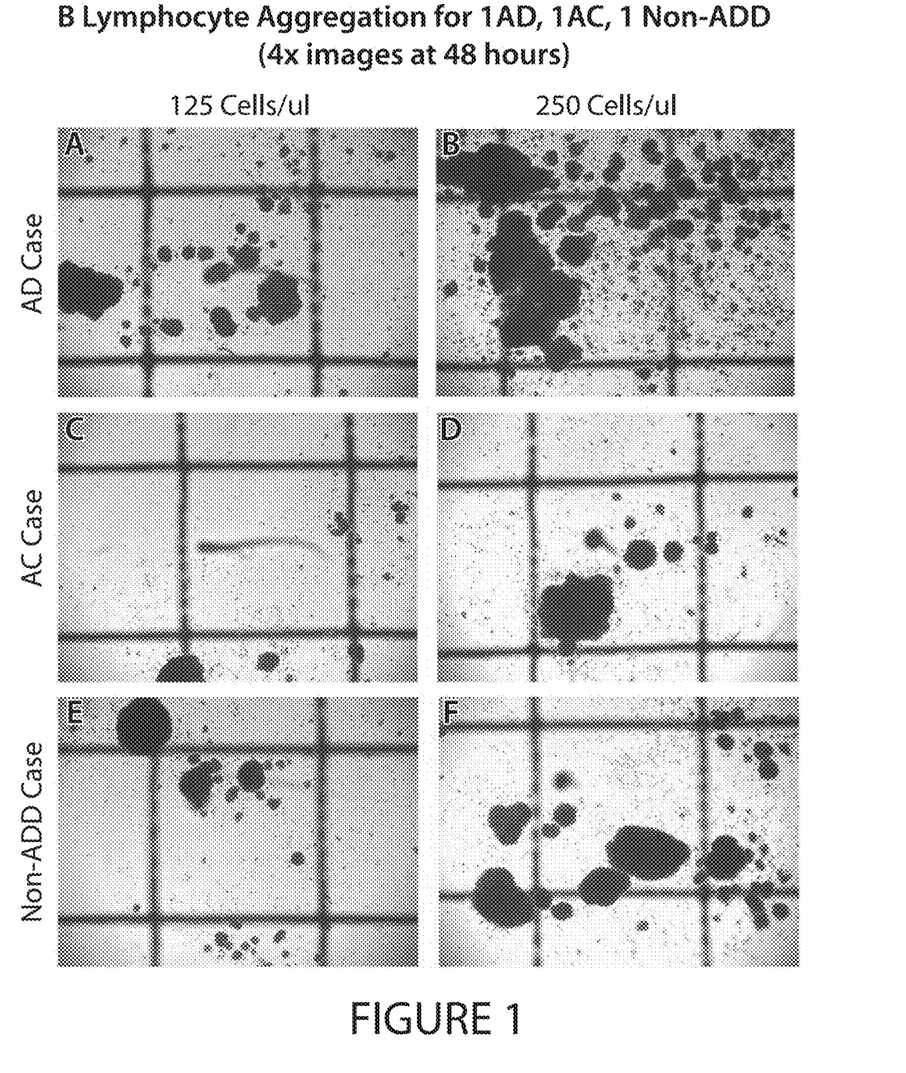
Figure 2A:
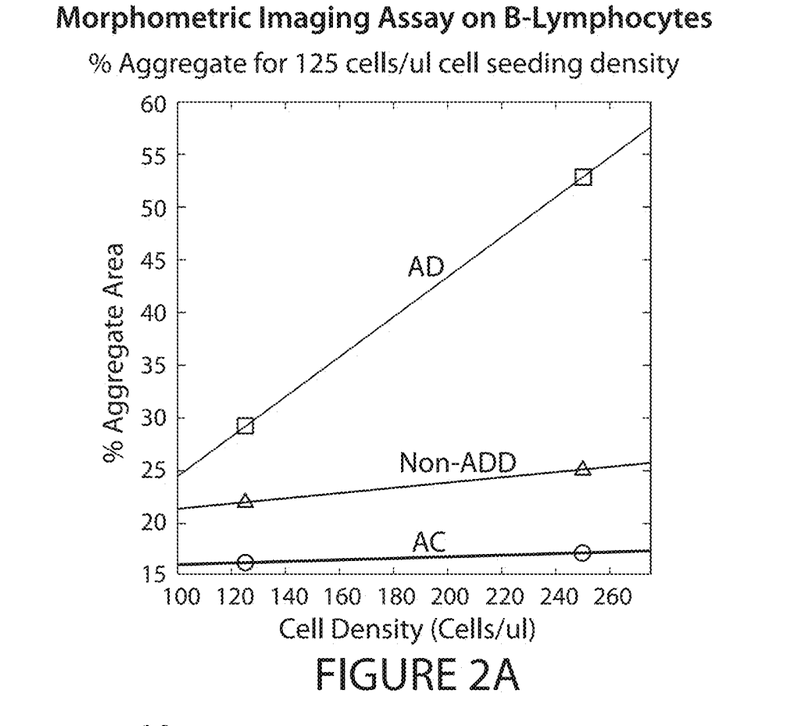
Figure 2B:
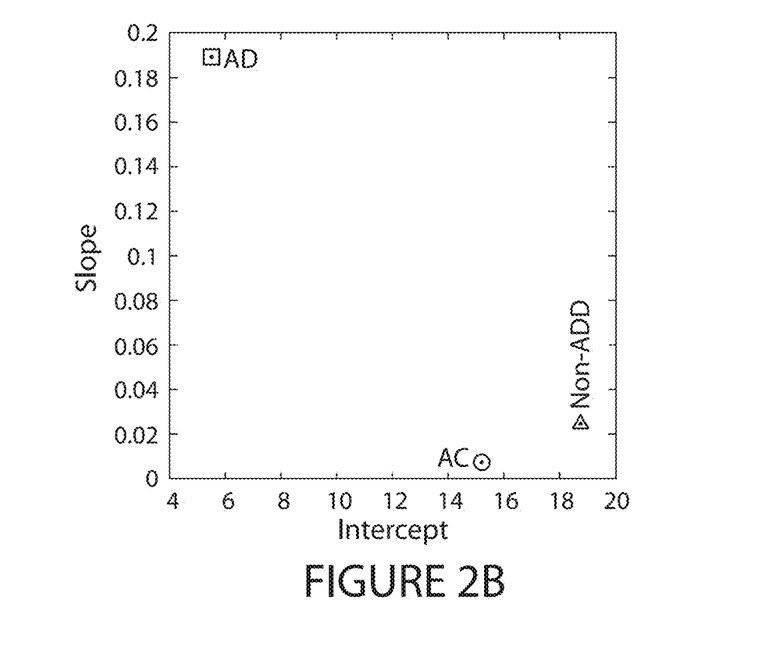
(FIG. 2B) The slopes and intercepts for the fit lines from A are represented here. The slope, representing the Aggregation Rate, is approximately 10-fold higher in the AD case when compared with the AC and Non-ADD cases.
Figure 3:
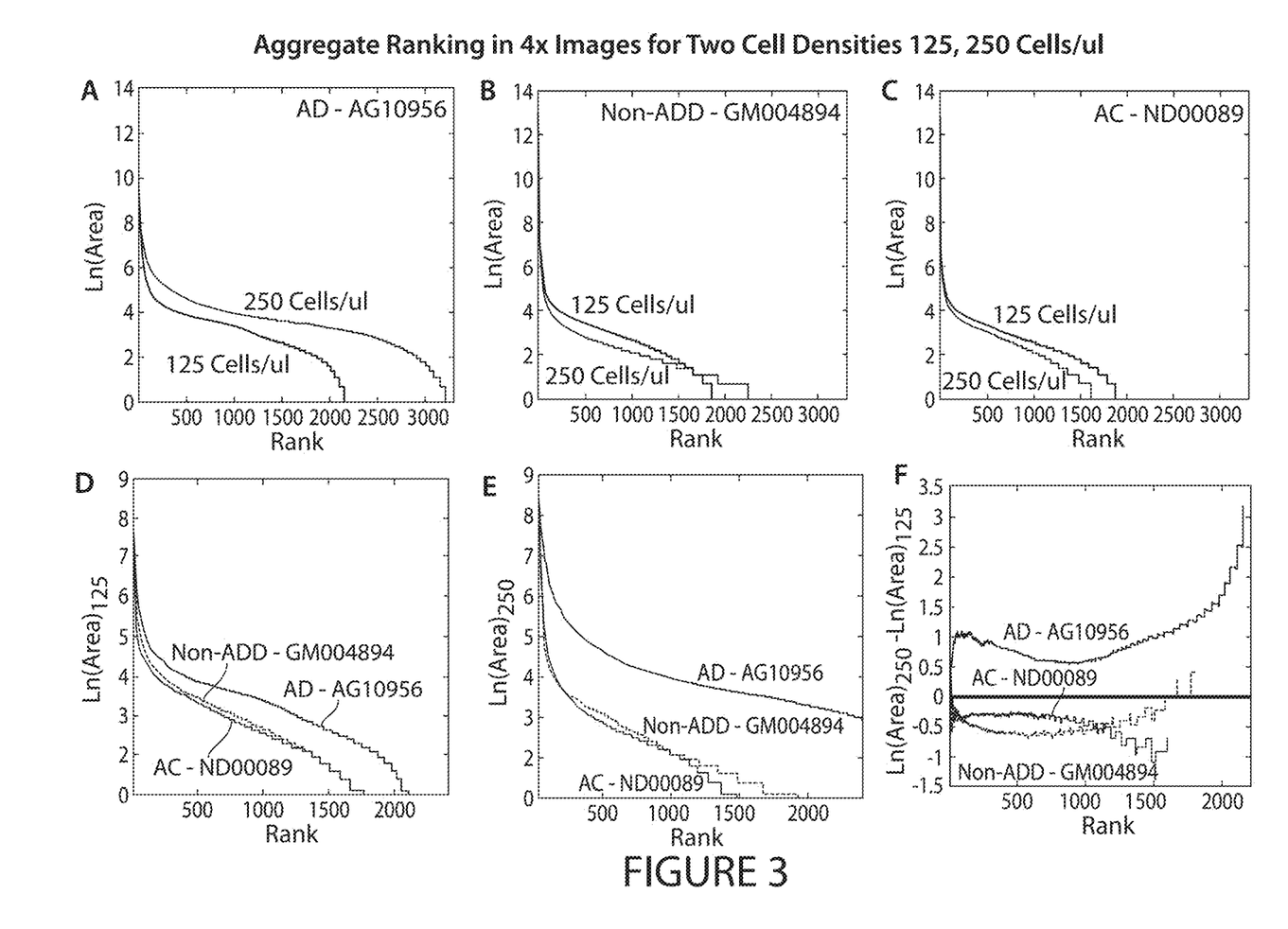
Figure 4:
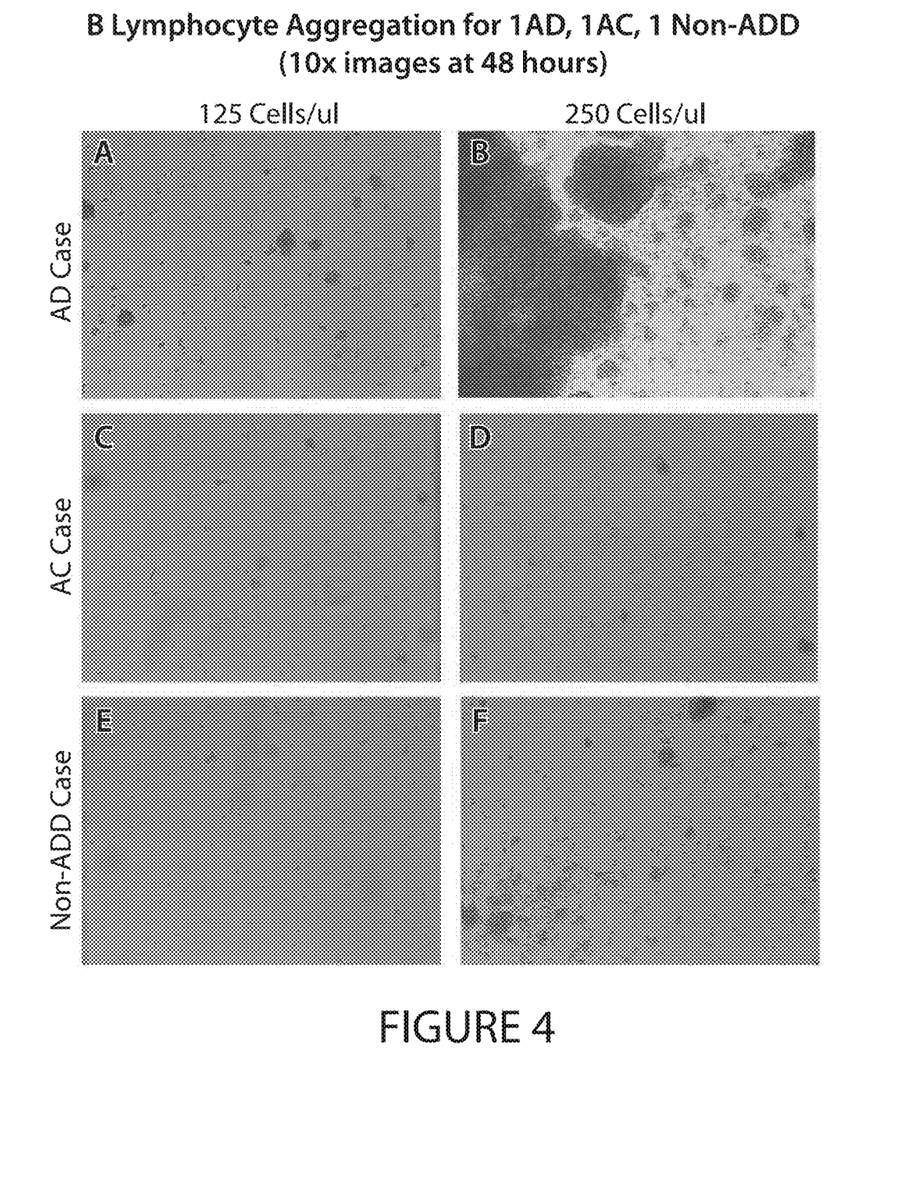
Figure 5A:
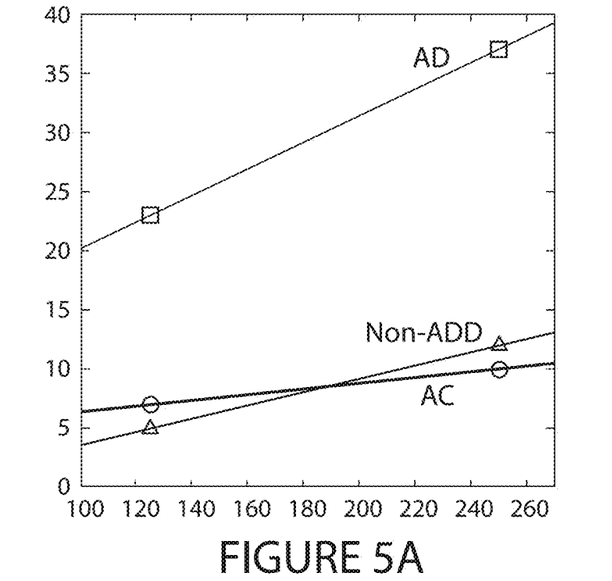
Figure 5B:
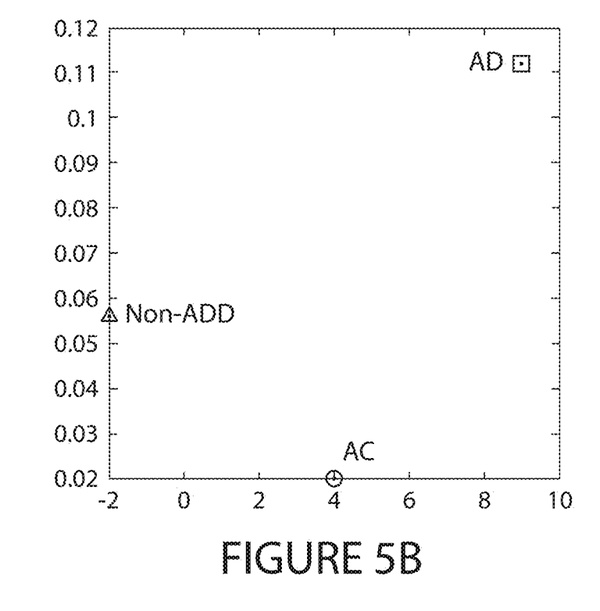
(FIG. 5B, bottom) The slopes and intercepts for the fit lines from (FIG. 5A) are represented here. The slope, representing the Aggregation Rate, is significantly higher in the AD case when compared with the AC and Non-ADD cases. Y-axis=slope; x-axis=intercept.

In this application, certain terms are used which shall have the meanings set forth as follows.

As used herein, "diagnosing Alzheimer's disease", with respect to a symptomatic human subject, means determining that there is greater than 50% likelihood that the subject is afflicted with Alzheimer's disease. Preferably, "diagnosing Alzheimer's disease" means determining that there is greater than 60%, 70%, 80% or 90% likelihood that the subject is afflicted with Alzheimer's disease. As used herein, the phrase "determining whether the subject is afflicted with Alzheimer's disease" is synonymous with the phrase "diagnosing Alzheimer's disease."

As used herein, "determining whether a human subject is predisposed to becoming afflicted with Alzheimer's disease" means determining that there is a greater than average likelihood that the subject will become afflicted with Alzheimer's disease during her or his lifetime. After the age of 65, one in five individuals will become afflicted with Alzheimer's disease, and after the age of 85, one in two individuals will become afflicted with Alzheimer's disease. Preferably, determining this predisposition means determining that there is at least a 20% likelihood that the subject will become afflicted with Alzheimer's disease during her or his lifetime.

As used herein, "Alzheimer's disease" means a concurrent affliction with the following three symptoms: (i) dementia; (ii) amyloid plaques; and (iii) neurofibrillary tangles. Dementia can be diagnosed during life. Cerebral amyloid plaques and neurofibrillary tangles can, for example, be diagnosed during autopsy. This definition of Alzheimer's disease is the one provided by the National Institute of Neurological Disorders and Stroke (NINDS) of the National Institutes of Health (NIH), and is known as the "gold standard."

As used herein, a human subject who is "symptomatic" for Alzheimer's disease is a subject displaying at least one symptom of the disease, i.e., one of dementia, amyloid plaques, and neurofibrillary tangles. Preferably, a human subject who is symptomatic for Alzheimer's disease is a subject displaying dementia. Conversely, a human subject who is "asymptomatic" for Alzheimer's disease is a subject who does not display any symptom of the disease.

As used herein, the "human subject" can be of any age. In one embodiment, the subject is 40 years old or younger. In another embodiment, the subject is 50 years old or younger. In a further embodiment, the subject is over 40 years old. In yet a further embodiment, the subject is over 50 years old, over 60 years old, over 70 years old, over 80 years old, or over 90 years old.

As used herein, "lymphocytes" include, by way of example, B lymphocytes, T lymphocytes, and mixtures thereof. Preferably, the lymphocytes are B lymphocytes. Methods for obtaining lymphocytes from a subject's blood are known, and include, for example, flow cytometry, Ficoll (a hydrophilic polysaccharide that separates layers of blood), and gradient centrifugation. A flow cytometry-based method is exemplified below. Additionally, in the subject methods, the lymphocytes (e.g., B lymphocytes) can be used in immortalized or primary (i.e., non-immortalized) form.

Methods for immortalizing lymphocytes (e.g., B lymphocytes) are known, and include, for example, treating the lymphocytes with Epstein-Barr virus ("EBV"). An EBV-based method is exemplified below.

As used herein, a "suitable basement membrane matrix" is any solid or semisolid matrix (e.g., a gel matrix) useful for permitting the growth of cells thereon and/or therein. Such cell growth includes, without limitation, cell division, cell enlargement, change in cell morphology, and formation of cell-cell attachments. Such matrices are known and include, without limitation, Matrigel®, Collagen I and IV, laminin, heparan sulfate proteoglycans, and entactin. Matrigel® and other matrices such as laminin and collagen facilitate cell growth.

As used herein, culturing lymphocytes with a suitable basement membrane matrix "for a duration and under conditions sufficient to permit the lymphocytes to aggregate" is achieved, for example, by conducting the culturing (i) for a duration of at least 30 minutes; (ii) at a temperature and in a growth factor milieu permissive of cell growth; and (iii) at a cell density that, at the beginning of culturing, permits at least some of the lymphocytes to be in physical contact with other lymphocytes. In one embodiment, the culturing is conducted for at least 30 minutes and no longer than 48 hours. In another embodiment, the temperature and protein milieu permissive of cell growth is 37° C., RPM 1640 Medium with 10% fetal bovine serum ("FBS") and 1% penicillin ("PS"), in the presence of growth factor-reduced ("GFR") Matrigel® (Corning, N.Y.).

As used herein, culturing lymphocytes "from" a subject means culturing lymphocytes originating from the subject, wherein prior to culturing, the lymphocytes either have or have not been manipulated (e.g., isolated, immortalized and/or otherwise modified) following removal from the subject.

In a preferred embodiment, the subject methods employ contacting a known quantity of matrix (e.g., 750 µl, 500 µl, 250 µl, 150 µl or 75 µl of Matrigel® in an assay well) with a known quantity of solution that contains a known quantity of lymphocytes to be tested. This lymphocyte-containing solution is described as having a particular "density" of lymphocytes per unit volume of solution (e.g., 125 cells/µl or 250 cells/µl). Once placed in contact with the matrix, lymphocytes in this solution of known cell density can contact, and affix themselves to, the matrix's surface and interior, to the extent the matrix's porosity permits. Cell densities that, at the beginning of culturing, permit at least some of the lymphocytes to be in physical contact with other lymphocytes include, without limitation, densities between 50 cells/µl and 500 cells/µl.

As used herein, lymphocyte "aggregation" means the physical attachment of at least one lymphocyte to at least one other lymphocyte. This attachment can be covalent or non-covalent. Moreover, for example, the attachment can involve one or more cell-cell interactions such as membrane adhesion, membrane fusion, and cell-cell fusion. It is noted that under the conditions envisioned for the subject methods, lymphocyte aggregation occurs both with lymphocytes from a subject afflicted with Alzheimer's disease and with lymphocytes from an un-afflicted subject. Under these conditions, however, the degree of aggregation differs between such lymphocyte populations. This unexpected difference, at least in part, underlies the utility of the subject methods.

As used herein, "measuring" lymphocyte aggregation can be performed, for example, using any method by which combined two-dimensional aggregate area can be determined, or by which combined aggregate volume can be determined. In a preferred embodiment, and as exemplified herein, lymphocyte aggregation is measured by determining the combined two-dimensional aggregate area as a percent fraction of the total matrix area examined. For example, in this scenario, a lymphocyte aggregation measurement of "50% aggregate area" means that when the matrix-containing assay well is viewed vertically, aggregated lymphocytes (that are readily visualized as such) occupy 50% of the assay well's area. This type of measurement does not factor in the combined aggregate volume or the combined surface area of the aggregates per se. In further embodiments, measuring lymphocyte aggregation includes determining total aggregation at a single time point (e.g., at 10 minutes, 20 minutes, 30 minutes, one hour, two hours, four hours, eight hours, 12 hours, 24 hours or 48 hours), and/or at multiple time points (e.g., at zero hours, 10 minutes, 20 minutes, 30 minutes, one hour, two hours, four hours, eight hours, 12 hours, 24 hours and 48 hours). Thus, the measurement can be of total lymphocyte aggregation (as measured, for example, by aggregation area) at a given time point, and/or of the rate of lymphocyte aggregate formation as derived from measurements taken during at least two time points.

Also envisioned is measuring lymphocyte aggregation by, and/or in conjunction with, one or more of the following methods disclosed in U.S. Pat. No. 8,658,134 (incorporated herein by reference): (i) determining an integrated score; (ii) determining the average aggregate area per number of aggregates; (iii) performing a cell migration analysis; (iv) performing a fractal analysis; and (v) performing a lacunarity analysis. In conjunction with one or more of these methods, the following steps are also envisioned: measuring cell and/or aggregate morphology characteristics such as the presence or absence of big clumps, the presence or absence of cells attached to the clumps, the presence or absence of big clumps growing, the number of clumps, the presence or absence of remnant edges from a previously formed network of the clumps, the number of cells migrating, the presence or absence of cells being near percolation, the number of cell clumps, the size of cell clumps, and the growth of cell clumps.

As used herein, a "suitable control" for performing the subject methods requiring same includes, without limitation, a positive control, a negative control, or one or more of each. For example, a positive control could be lymphocyte aggregation data obtained by performing one of the subject methods on lymphocytes obtained from a human subject afflicted with Alzheimer's disease. A negative control could be, for example, lymphocyte aggregation data obtained by performing one of the subject methods on lymphocytes obtained from a human subject who is not afflicted with Alzheimer's disease (e.g., a subject without any cognitive symptoms, a subject afflicted with mild cognitive impairment, or a subject afflicted with non-Alzheimer's dementia). Importantly, it is envisioned that in some of the subject methods, control tests (e.g., positive, negative and/or both) will be performed before, concurrently with or after testing the lymphocytes from the human subjects of interest. The data from such control tests can then serve as suitable controls. It is also envisioned that in other of the subject methods, no control tests are performed before, concurrently with or after testing the lymphocytes from the human subjects of interest. Instead, in each such method, determining affliction with, or predisposition to, Alzheimer's disease (as applicable) can be achieved, for example, by comparing the method's result with lymphocyte aggregation parameters (e.g., 50% area at a lymphocyte density of 250 cells/µl and a duration of 48 hours) having a known correlation with disease state or predisposition, as applicable.

EMBODIMENTS OF THE INVENTION

This invention provides lymphocyte-based methods for diagnosing Alzheimer's disease in a human subject. It also provides lymphocyte-based methods for determining whether a human subject is predisposed to becoming afflicted with Alzheimer's disease. The subject methods are based, at least in part, on the surprising discovery that a subject's lymphocytes can be used in a morphometric test to either diagnose Alzheimer's disease or determine a predisposition to Alzheimer's disease, as applicable.

Specifically, this invention provides a first method, namely, a method for diagnosing Alzheimer's disease in a symptomatic human subject comprising the steps of (a) culturing lymphocytes from the subject with a suitable basement membrane matrix for a duration and under conditions sufficient to permit the lymphocytes to aggregate; (b) measuring the resulting lymphocyte aggregation; and (c) comparing the measurement of step (b) with a suitable control, thereby determining whether the subject is afflicted with Alzheimer's disease.

In this first method and the second, third and fourth methods described below, the lymphocytes can be any type of lymphocytes. Preferably, the lymphocytes are B lymphocytes. Also preferred are B lymphocytes that are immortalized. Basement membrane matrices suitable for use in this first method, and the second, third and fourth methods described below, are numerous and commercially available. In the preferred embodiment, the suitable basement membrane matrix is Matrigel®.

In this first method and the second, third and fourth methods described below, the lymphocyte density is high enough to permit the required aggregation, and low enough so that the aggregation does not exceed the amount permitting meaningful results. In one embodiment, the lymphocyte density is between 50 cells/µl and 500 cells/µl. In another embodiment, the lymphocyte density is between 50 cells/µl and 100 cells/µl, 100 cells/µl and 150 cells/µl, 150 cells/µl and 200 cells/µl, 200 cells/µl and 250 cells/µl, 250 cells/µl and 300 cells/µl, 300 cells/µl and 350 cells/µl, 350 cells/µl and 400 cells/µl, 400 cells/µl and 450 cells/µl, and 450 cells/µl and 500 cells/µl. In a further embodiment, the lymphocyte density is 50 cells/µl, 100 cells/µl, 150 cells/µl, 200 cells/µl, 250 cells/µl, 300 cells/µl, 350 cells/µl, 400 cells/µl, 450 cells/µl or 500 cells/µl.

In this first method and the second, third and fourth methods described below, the duration sufficient to permit the lymphocytes to aggregate is long enough to permit the required aggregation, and brief enough so that the aggregation does not exceed the amount permitting meaningful results. In the preferred embodiment, the duration sufficient to permit the lymphocytes to aggregate is between 30 minutes and 48 hours. In a further embodiment, the duration sufficient to permit the lymphocytes to aggregate is between 30 minutes and two hours, 30 minutes and four hours, 30 minutes and eight hours, 30 minutes and 12 hours, 30 minutes and 24 hours, two hours and four hours, two hours and eight hours, two hours and 12 hours, two hours and 24 hours, two hours and 48 hours, four hours and eight hours, four hours and 12 hours, four hours and 24 hours, four hours and 48 hours, eight hours and 12 hours, eight hours and 24 hours, eight hours and 48 hours, 12 hours and 24 hours, 12 hours and 48 hours, and 24 hours and 48 hours.

In a preferred embodiment of the first method, this invention provides a method for diagnosing Alzheimer's disease in a symptomatic human subject comprising the steps of (a) culturing immortalized B lymphocytes from the subject with Matrigel® for between 30 minutes and 48 hours at a lymphocyte density between 50 cells/µl and 500 cells/µl; (b) measuring the resulting lymphocyte aggregation; and (c) comparing the measurement of step (b) with a suitable control, thereby determining whether the subject is afflicted with Alzheimer's disease.

This invention also provides a second method, namely, a method for determining whether a human subject is predisposed to becoming afflicted with Alzheimer's disease comprising the steps of (a) culturing lymphocytes from the subject with a suitable basement membrane matrix for a duration and under conditions sufficient to permit the lymphocytes to aggregate; (b) measuring the resulting lymphocyte aggregation; and (c) comparing the measurement of step (b) with a suitable control, thereby determining whether the subject is predisposed to becoming afflicted with Alzheimer's disease.

In this second method and the fourth method described below, the subject may be afflicted with a cognitive disability. In one embodiment, this disability is mild cognitive impairment. Alternatively, in this second method and the fourth method described below, the subject is not cognitively impaired.

In a preferred embodiment of the second method, this invention provides a method for determining whether a human subject is predisposed to becoming afflicted with Alzheimer's disease comprising the steps of (a) culturing immortalized B lymphocytes from the subject with Matrigel® for between 30 minutes and 48 hours at a lymphocyte density between 50 cells/µl and 500 cells/µl; (b) measuring the resulting lymphocyte aggregation; and (c) comparing the measurement of step (b) with a suitable control, thereby determining whether the subject is predisposed to becoming afflicted with Alzheimer's disease.

This invention further provides a third method, namely, a method for diagnosing Alzheimer's disease in a symptomatic human subject comprising the steps of (a) culturing lymphocytes from the subject with a suitable basement membrane matrix for a duration and under conditions sufficient to permit the lymphocytes to aggregate; (b) measuring the resulting lymphocyte aggregation; and (c) determining whether the measurement of step (b) correlates with Alzheimer's disease in the subject.

In this third method, measuring the resulting lymphocyte aggregation comprises measuring the percent aggregate area, and determining whether that percent aggregate area correlates with the percent aggregate area expected in a subject afflicted with Alzheimer's disease.

In a preferred embodiment of the third method, this invention provides a method for diagnosing Alzheimer's disease in a symptomatic human subject comprising the steps of (a) culturing immortalized B lymphocytes from the subject with Matrigel® for between 30 minutes and 48 hours at a lymphocyte density between 50 cells/µl and 500 cells/µl; (b) measuring the resulting lymphocyte aggregation; and (c) determining whether the measurement of step (b) correlates with Alzheimer's disease in the subject.

Finally, this invention provides a fourth method, namely, a method for determining whether a human subject is predisposed to becoming afflicted with Alzheimer's disease comprising the steps of (a) culturing lymphocytes from the subject with a suitable basement membrane matrix for a duration and under conditions sufficient to permit the lymphocytes to aggregate; (b) measuring the resulting lymphocyte aggregation; and (c) determining whether the measurement of step (b) correlates with the subject's being predisposed to becoming afflicted with Alzheimer's disease.

In this fourth method, measuring the resulting lymphocyte aggregation can be achieved via any suitable approach. In the preferred embodiment, measuring the resulting lymphocyte aggregation comprises measuring the percent aggregate area, and determining whether that percent aggregate area correlates with the percent aggregate area expected in a subject predisposed to becoming afflicted with Alzheimer's disease.

In a preferred embodiment of the fourth method, this invention provides a method for determining whether a human subject is predisposed to becoming afflicted with Alzheimer's disease comprising the steps of (a) culturing immortalized B lymphocytes from the subject with Matrigel® for between 30 minutes and 48 hours at a lymphocyte density between 50 cells/µl and 500 cells/µl; (b) measuring the resulting lymphocyte aggregation; and (c) determining whether the measurement of step (b) correlates with the subject's being predisposed to becoming afflicted with Alzheimer's disease.

This invention further provides a kit for performing any of the subject methods, wherein the kit comprises, in separate compartments or a single compartment, (i) a growth medium (e.g., RPMI 1640 Medium with 10% FBS and 1% PS) and (ii) a basement membrane matrix (e.g., Matrigel® or other 3D matrix such as collagen or laminin), wherein the growth medium and matrix together permit lymphocyte aggregation under suitable conditions.

This invention still further provides a composition of matter comprising aggregated lymphocytes (e.g., EBV-immortalized B lymphocytes) and a suitable basement membrane matrix (e.g., Matrigel®).

Also envisioned is the application of the instant invention to (i) any non-lymphocyte peripheral blood mononuclear cell (PBMC) and (ii) any pluripotent stem cell (iPSC) derived from a reprogrammed EBV-immortalized B lymphocyte (https://www.ncbi.nlm.nih.gov/pmc/articles/PMC3158714/; and https://www.ncbi.nlm.nih.gov/pmc/articles/PMC2596471/). In this embodiment, such cells are treated, mutatis mutandis, as lymphocytes are treated in this invention.

Further envisioned is the application of each of the instant diagnostic methods, but without the step of explicitly comparing the subject's lymphocyte aggregation measurement with a suitable control. That is, this invention provides a version of each of the four instant diagnostic methods wherein the subject's lymphocyte aggregation measurement either does or does not meet a pre-determined threshold indicative of Alzheimer's disease.

This invention will be better understood by reference to the examples which follow, but those skilled in the art will readily appreciate that the specific examples detailed are only illustrative of the invention as described more fully in the claims which follow thereafter.

EXAMPLE 1

PBMC Preparation. Whole blood, sampled in BD Vacutainer CPT™ Cell Preparation Tubes with sodium heparin (BD Bioscience, Franklin Lakes, N.J., USA), was diluted 1:2 in PBS and gently layered over cold Ficoll-Paque PLUS (GE Healthcare, Little Chalfont, UK) and kept on ice before centrifugation for 20 min at 900×g without brake at 18-20° C. The cell layer on top of the Ficoll-Paque PLUS consisting of peripheral blood mononuclear cells (PBMCs) was collected and diluted in PBS. PBMCs were centrifuged again for 7 min at 450×g at 18-20° C. The supernatant was removed and cells were re-suspended in 5 ml PBS and counted before they were centrifuged at 350×g for seven min at 18-20° C. Finally, cells were re-suspended in freezing medium (10% DMSO in heat-inactivated fetal bovine serum (FBS) (Nordic Biolabs Aft Taby, Sweden) and placed at −70° C. in a Mr. Frosty™ Freezing Container (Thermo Fisher) for at least three hours before being transferred to liquid nitrogen for extended storage.

Flow Cytometry. For each individual cell sample, $5 \times 10^6$ PBMCs were quickly thawed at 37° C. and diluted in 40 ml cold wash buffer (PBS supplemented with 2.5% FBS (Life Technologies Ltd. Paisley, UK) and 0.1% sodium azide). The cell suspension was centrifuged at 250×g for five min and after discarding the supernatant, the pellet was re-suspended in 400 ml wash buffer. Each sample was stained for one hour in a light-protected environment at 2° C. with titrated amounts of anti-CD19 labeled with Alexa Fluor 700 (BD Biosciences). Samples were analyzed using a BD LSR II Special Order System, controlled by the BD FACSDiva 6.0 software (BD Biosciences). A preliminary forward scatter (FSC) versus side scatter (SSC) gate was used to identify lymphocytes and, depending on sample size, a total of up to 100,000 in-gate events were recorded. All datasets were migrated to FlowJo 7.6.5 (Treestar Inc. Ashland, Oreg., USA) for further gating and analysis.

Cells were cultured as per Coriell Cell Repository specifications, i.e., at 37° C., in water jacket $CO_2$ incubators in RPMI 1640 Medium, with 10% FBS and 1% PS. The Growth Factor Reduced (GFR) Matrigel® from Corning was thawed overnight at +4° C. and 750 µl/well was used. A 30-minute incubation at 37° C. was used before cell seeding.

EXAMPLE 2

The inaccuracy of existing diagnostic methods for Alzheimer's disease has made therapeutic intervention difficult. This is particularly true regarding therapeutic intervention that is early enough to prevent significant neurodegeneration and cognitive dysfunction.

The instant invention provides accurate diagnostic methods for patients suspected of having Alzheimer's disease. These methods involve quantitatively measuring aggregation rates of human immortalized B lymphocytes. A basis of this invention is elevated in vitro lymphocyte aggregation (i.e., the "biomarker" measured here) correlative with increasing lymphocyte density in Alzheimer's disease.

This new biomarker was successfully validated with a different assay based on the imbalances of a second, different biomarker, and showed complete diagnostic overlap with the second biomarker.

The lymphocytes tested using the subject methods were banked cells from the Coriell Cell Repository. The disease-related "pedigrees" of these banked cells were validated via autopsy and/or were genetically confirmed as Alzheimer's patients (AD) or non-Alzheimer's demented patients (Non-ADD) and non-demented age-matched controls (AC).

Given the accuracy of the subject methods, they are valuable for diagnosing Alzheimer's disease and thereby permitting timely therapeutic intervention.

What is claimed is:

1. A method for diagnosing Alzheimer's disease in a symptomatic human subject comprising the steps of (a) culturing B lymphocytes from the subject with a suitable basement membrane matrix for a duration and under conditions sufficient to permit the lymphocytes to aggregate; (b) measuring the percent aggregate area of the resulting lymphocyte aggregation; and (c) comparing the measurement of step (b) with a suitable control, thereby determining whether the subject is afflicted with Alzheimer's disease, wherein the culturing step (a) comprises seeding the lymphocytes at a density between 125 cells/µl and 250 cells/µl.

2. The method of claim 1, wherein the B lymphocytes are immortalized.

3. The method of claim 1, wherein the suitable basement membrane matrix is Matrigel.

4. The method of claim 1, wherein the duration sufficient to permit the lymphocytes to aggregate is between 30 minutes and 48 hours.

5. A method for diagnosing Alzheimer's disease in a symptomatic human subject comprising the steps of (a) culturing immortalized B lymphocytes from the subject with Matrigel for between 30 minutes and 48 hours at a lymphocyte cell seeding density between 125 cells/µl and 250 cells/µl; (b) measuring the percent aggregate area of the resulting lymphocyte aggregation; and (c) comparing the measurement of step (b) with a suitable control, thereby determining whether the subject is afflicted with Alzheimer's disease.

6. The method of claim 1, wherein the lymphocyte cell seeding density is 125 cells/µl.

7. The method of claim 1, wherein the lymphocyte cell seeding density is 250 cells/µl.

8. The method of claim 5, wherein the lymphocyte cell seeding density is 125 cells/µl.

9. The method of claim 5, wherein the lymphocyte cell seeding density is 250 cells/µl.

* * * * *